(12) United States Patent
Burroughs, III

(10) Patent No.: US 8,894,676 B2
(45) Date of Patent: Nov. 25, 2014

(54) TUBULAR LIGAMENT CUTTING IMPLEMENT

(71) Applicant: Paul Leach Burroughs, III, Raleigh, NC (US)

(72) Inventor: Paul Leach Burroughs, III, Raleigh, NC (US)

( * ) Notice: Subject to any disclaimer, the term of this patent is extended or adjusted under 35 U.S.C. 154(b) by 0 days.

(21) Appl. No.: 13/832,638

(22) Filed: Mar. 15, 2013

(65) Prior Publication Data

US 2013/0331877 A1 Dec. 12, 2013

Related U.S. Application Data

(63) Continuation-in-part of application No. 13/493,320, filed on Jun. 11, 2012.

(51) Int. Cl.
*A61B 17/32* (2006.01)
*A61B 17/00* (2006.01)

(52) U.S. Cl.
CPC ........... *A61B 17/320016* (2013.01); *A61B 2017/00969* (2013.01)
USPC ............................................... 606/170

(58) Field of Classification Search
CPC ........... A61B 17/32002; A61B 17/320758; A61B 2217/005; A61B 10/0266; A61B 17/320016; A61B 10/0275; A61B 17/320783; A61B 2017/320775; A61B 2017/320024; A61F 9/00763
USPC .......... 600/564, 565, 566, 567; 606/110, 114, 606/115, 167, 168, 169, 170, 171, 172, 606/180; 30/114, 115, 116, 117; 83/196, 83/199
See application file for complete search history.

(56) References Cited

U.S. PATENT DOCUMENTS

| | | | |
|---|---|---|---|
| 622,461 A | | 4/1899 | Glardon-Jacquet et al. |
| 3,583,390 A | | 6/1971 | Jascalevich |
| 3,815,604 A | * | 6/1974 | O'Malley et al. ............... 604/22 |
| 3,844,272 A | * | 10/1974 | Banko ........................... 600/566 |
| 3,902,498 A | * | 9/1975 | Niederer ....................... 606/170 |
| 4,099,529 A | * | 7/1978 | Peyman ....................... 606/171 |
| 4,461,305 A | * | 7/1984 | Cibley ........................... 600/567 |
| 4,696,298 A | * | 9/1987 | Higgins et al. ................ 606/171 |
| 4,832,045 A | | 5/1989 | Goldberger |
| 4,985,031 A | | 1/1991 | Buss et al. |
| 5,007,917 A | * | 4/1991 | Evans ........................... 606/170 |
| 5,112,299 A | * | 5/1992 | Pascaloff ........................ 604/22 |
| 5,226,910 A | * | 7/1993 | Kajiyama et al. ............. 606/171 |
| 5,267,572 A | * | 12/1993 | Bucalo ........................... 600/567 |

(Continued)

FOREIGN PATENT DOCUMENTS

WO 2008019097 A2 2/2008

OTHER PUBLICATIONS

Non-final Office Action for U.S. Appl. No. 13/102,562 mailed Oct. 15, 2013, 14 pages.

(Continued)

*Primary Examiner* — Jonathan W Miles

(74) *Attorney, Agent, or Firm* — Withrow & Terranova, P.L.L.C.

(57) ABSTRACT

A cutting implement includes a first tubular portion and a second tubular portion. Each tubular portion is hollow and includes a blade element at a distal end. The blade element helps define an aperture that allows access to the interior hollow portion of the tubular portion. A ligament graft element is threaded through the aperture of each tubular portion and the respective tubular portions are interoperated to cut the ligament graft.

10 Claims, 12 Drawing Sheets

(56) References Cited

U.S. PATENT DOCUMENTS

| | | | | |
|---|---|---|---|---|
| 5,269,798 | A | * | 12/1993 | Winkler .................... 606/170 |
| 5,285,795 | A | * | 2/1994 | Ryan et al. .................. 600/563 |
| 5,346,497 | A | * | 9/1994 | Simon et al. ................ 606/107 |
| 5,391,169 | A | | 2/1995 | McGuire |
| 5,505,210 | A | * | 4/1996 | Clement ..................... 600/566 |
| 5,549,618 | A | * | 8/1996 | Fleenor et al. .............. 606/148 |
| 5,570,700 | A | | 11/1996 | Vogeler |
| 5,630,826 | A | * | 5/1997 | Sastri ........................ 606/170 |
| 5,720,760 | A | * | 2/1998 | Becker et al. ............... 606/180 |
| 5,722,977 | A | | 3/1998 | Wilhelmy |
| 5,807,277 | A | * | 9/1998 | Swaim ....................... 600/567 |
| 5,893,862 | A | * | 4/1999 | Pratt et al. .................. 606/170 |
| 5,933,968 | A | | 8/1999 | Solomon |
| 6,033,375 | A | * | 3/2000 | Brumbach ................... 604/22 |
| 6,035,536 | A | | 3/2000 | Dewberry |
| 6,053,928 | A | * | 4/2000 | Van Wyk et al. ............ 606/167 |
| 6,258,094 | B1 | | 7/2001 | Nicholson et al. |
| 6,391,031 | B1 | | 5/2002 | Toomey |
| 7,285,122 | B2 | | 10/2007 | Sanford et al. |
| 8,088,135 | B2 | * | 1/2012 | Heisler ....................... 606/171 |
| 8,177,803 | B2 | * | 5/2012 | Heisler ....................... 606/171 |
| 8,308,746 | B2 | * | 11/2012 | Pravong et al. .............. 606/169 |
| 8,551,101 | B2 | | 10/2013 | Kuczynski |
| 2004/0102772 | A1 | * | 5/2004 | Baxter et al. ................. 606/45 |
| 2005/0149092 | A1 | | 7/2005 | Dunn |
| 2006/0004397 | A1 | * | 1/2006 | Osawa ........................ 606/180 |
| 2006/0212057 | A1 | | 9/2006 | Djordjevic et al. |
| 2006/0212060 | A1 | * | 9/2006 | Hacker et al. ............... 606/180 |
| 2008/0021487 | A1 | * | 1/2008 | Heisler ....................... 606/170 |
| 2008/0065113 | A1 | | 3/2008 | Smith |
| 2008/0161810 | A1 | | 7/2008 | Melkent |
| 2009/0048485 | A1 | | 2/2009 | Heisler |
| 2010/0069944 | A1 | | 3/2010 | Murakami et al. |
| 2011/0004214 | A1 | | 1/2011 | Skaggs |
| 2011/0087260 | A1 | | 4/2011 | Seipel et al. |
| 2011/0306483 | A1 | | 12/2011 | Valente |
| 2012/0065658 | A1 | * | 3/2012 | Heisler ....................... 606/170 |
| 2012/0191121 | A1 | * | 7/2012 | Chen et al. .................. 606/180 |
| 2013/0331876 | A1 | | 12/2013 | Burroughs, III |

OTHER PUBLICATIONS

International Preliminary Report on Patentability for PCT/US2012/036728 mailed Nov. 21, 2013, 6 pages.

Non-final Office Action for U.S. Appl. No. 13/493,320 mailed Dec. 23, 2013, 7 pages.

International Search Report and Written Opinion for PCT/US2013/044973 mailed Sep. 5, 2013, 12 pages.

International Search Report and Written Opinion for PCT/US2012/036728 mailed Nov. 23, 2012, 10 pages.

Author Unknown, "New or Refurbished—ValleyLab Force FX," DRE Inc, accessed on May 6, 2011, www.dremed.com/catalog/product_info.php/cPath/45_78/products_id/421, 1 page.

Author Unknown, "Cautery Electrodes," DRE Inc, accessed on May 6, 2011, www.orsupply.com/medical/category/Cautery+Electrodes/489, 3 pages.

International Preliminary Report on Patentability for PCT/US13/44973, mailed Jun. 4, 2014, 6 pages.

Final Office Action for U.S. Appl. No. 13/102,562, mailed May 8, 2014, 13 pages.

Final Office Action for U.S. Appl. No. 13/493,320, mailed May 15, 2013, 8 pages.

Advisory Action for U.S. Appl. No. 13/102,562, mailed Jul. 22, 2014, 3 pages.

Advisory Action for U.S. Appl. No. 13/493,320, mailed Jul. 17, 2014, 3 pages.

* cited by examiner

TUBULAR LIGAMENT CUTTING IMPLEMENT

PRIORITY APPLICATION

The present application is a continuation-in-part of U.S. patent application Ser. No. 13/493,320 ('320 application) filed Jun. 11, 2012. The contents of the '320 application are herein incorporated by reference in their entirety.

FIELD OF THE DISCLOSURE

The present disclosure relates to a cutting instrument adapted to help a surgeon harvest a replacement tendon for an anterior cruciate ligament (ACL) injury from the quadriceps tendon.

BACKGROUND

Most people can go through the majority of their life without ever appreciating the complicated structure of the knee that helps them walk. However, the knee remains a fragile mechanical structure that is readily susceptible to damage. While medical advances have made repairing the knee possible, repair of certain types of injuries results in other long term effects. To assist the reader, FIG. 1 is provided with a brief explanation of the components of the knee.

For the purposes of the present disclosure, and as illustrated, the knee may be composed of the quadriceps muscles 10, the femur 12, the articular cartilage 14, the lateral condyle 16, the posterior cruciate ligament 18, the anterior cruciate ligament 20, the lateral collateral ligament 22, the fibula 24, the tibia 26, the patellar tendon 28, the meniscus 30, the medial collateral ligament 32, the patella 34 (shown slightly displaced to the side—it normally rests in the center of the knee) and the quadriceps tendon 36. Of particular interest for the purposes of the present disclosure is the anterior cruciate ligament (ACL) 20 and what is done to repair the ACL 20.

ACL tears are common in athletes and are usually season ending injuries. The ACL 20 cannot heal—it must be surgically reconstructed. The reconstruction requires replacement tissue. The most common tissue used is a central slip of the patient's own patellar tendon 28. In practice, the patellar tendon 28 has proven to be generally effective, but the size of the graft that can be used is limited to the size of the patient's own patellar tendon 28. As a rule of thumb, only a third of the patellar tendon 28 may be harvested as a graft. Thus, a doctor will measure the width of the patellar tendon 28, divide by three, and take the middle third of the patellar tendon 28. Such harvested grafts are rarely more than 10 mm wide and may be smaller. Taking this tissue from a person's patellar tendon 28 also causes significant pain and discomfort in the post operative healing period, which may last up to a year, and up to twenty (20) percent of these patients are left with chronic anterior knee pain.

Some doctors recommend and use other graft sources, such as cadaver grafts, but cadaver grafts have a higher failure rate. Additionally, there is a non-zero chance of disease transmission or rejection by the patient's immune system. As a final drawback, cadaver grafts are usually quite expensive and may not be covered by some insurance companies.

Other doctors use hamstring tendons (e.g., the distal semitendinosus tendon) because the scar created during harvesting is relatively small and there is less pain during the rehabilitation, but again, the hamstring tendon has its own collection of disadvantages. The disadvantages include the fact that once the graft is taken, a patient's hamstring will never recover to its previous strength. Further, all hamstring reconstructions stretch and are looser than the original ACL 20. This loosening is particularly problematic in younger female athletes.

Another alternative graft source is the quadriceps tendon 36. The quadriceps tendon 36 is larger and stronger than either the patellar tendon 28 or the hamstring tendon. The quadriceps tendon 36 is likewise stiffer and less prone to stretching or plastic deformation. However, the qualities that make the quadriceps tendon 36 attractive also contribute to the difficulty in harvesting a graft from the quadriceps tendon 36. Existing surgical implements require a large incision up the longitudinal axis of the femur 12 on the front or ventral/anterior side of the thigh to cut down to the level of the quadriceps tendon 36, resulting in a large post operative scar. Additionally, the quadriceps tendon 36 has a consistency similar to the proverbial shoe leather, making it difficult to cut. However, an ACL 20 repaired with grafts from the quadriceps tendon 36 generally results in almost no anterior knee pain postoperatively over the short or long term and recovers quicker.

The present inventor's prior application, U.S. patent application Ser. No. 13/102,562 ('562 application), filed May 6, 2011 (which is hereby incorporated by reference in its entirety), provides a number of devices designed to create a graft from the quadriceps tendon 36 and discloses an element to make the initial cut on the quadriceps tendon 36 as well as a number of secondary cutting implements to trim the distal end of the graft. While these secondary cutting implements are adequate to perform their intended purpose, alternate devices may be more cost effective or have easier engineering realities. The previously incorporated '320 application also provides suitable secondary cutting implements, but again, alternate devices may be more cost effective, be more efficacious at cutting, or have easier engineering realities.

SUMMARY

The present disclosure provides a secondary cutting implement that is adapted to trim a distal end of a preliminarily harvested graft from the quadriceps tendon in a minimally invasive manner. Once the quadriceps tendon graft is secured, it may be used in conventional manners to repair the anterior cruciate ligament (ACL).

The secondary cutting implement comprises a first hollow tubular element and a second hollow tubular element that telescopingly fits within the first tubular element. The distal ends of each tubular element include an interior blade element positioned perpendicular to a longitudinal axis of the tubular element. The interior blade elements are sized such that the distal end of each tubular portion is at least partially open. That is, the blade elements help define an aperture at the distal end of the tubular hollow elements.

In use, the quadriceps tendon is cut to a desired length and then the graft portion is threaded through the open distal end of the first tubular element. The graft portion is also threaded through the open distal end of the second tubular element. The tubular elements are rotated in opposite directions causing the interior blade elements to trim the distal end of the graft.

An additional embodiment differs in that only a single one of the tubular elements has a blade. Likewise, the distal ends of the tubular elements include a cutaway or notch that facilitates insertion of the bone plug portion of the graft as the graft is threaded through the open distal end. Additionally, a third tubular element may be included that upon insertion closes the cutaway or notches in the first and second tubular elements to improve cutting when the notches are partially aligned.

While the present disclosure focuses on the use of the tubular cutting implement in the context of cutting quadriceps tendons for repairing ACL injuries, the present disclosure is not so limited, and the tubular cutting implement may be used in other sorts of procedures.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

Figure 1:
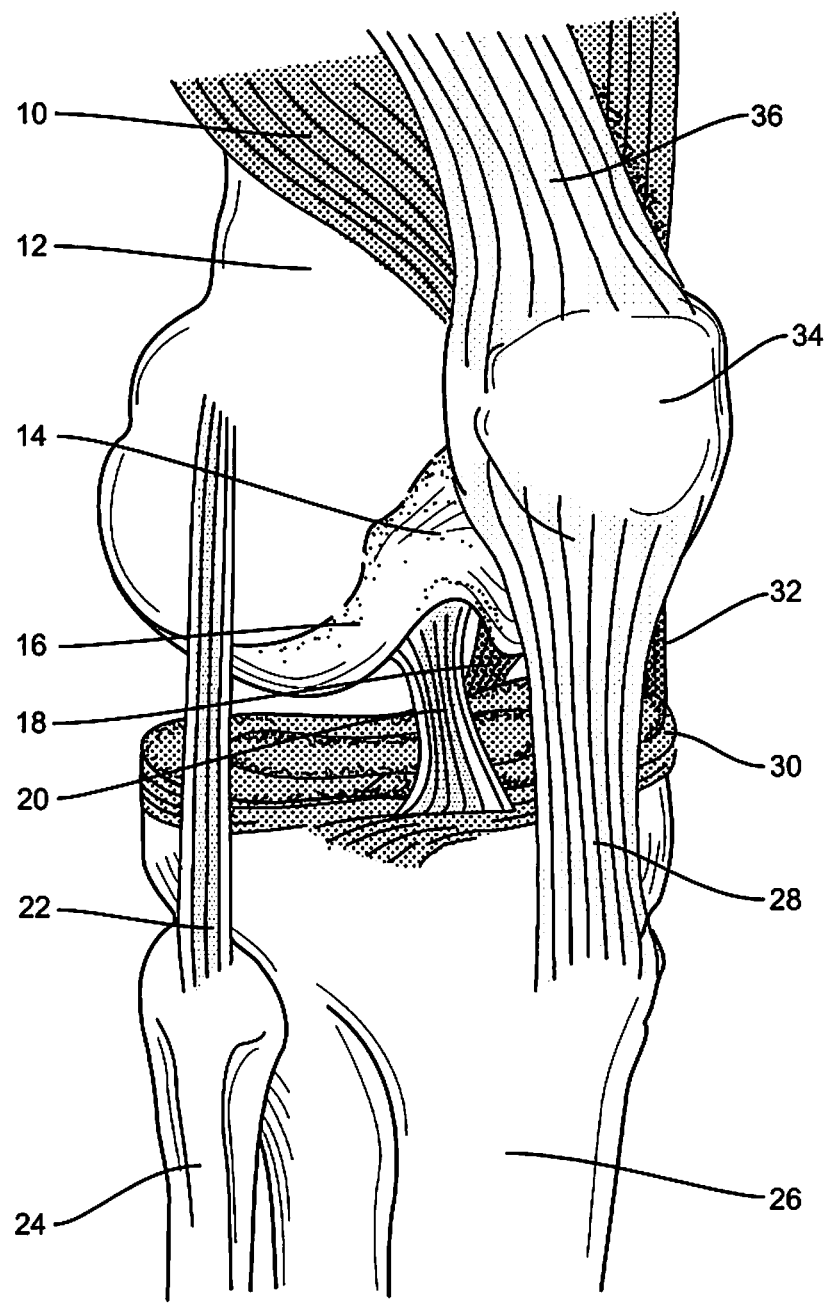
FIG. 1 illustrates a conventional knee.
Figure 2:
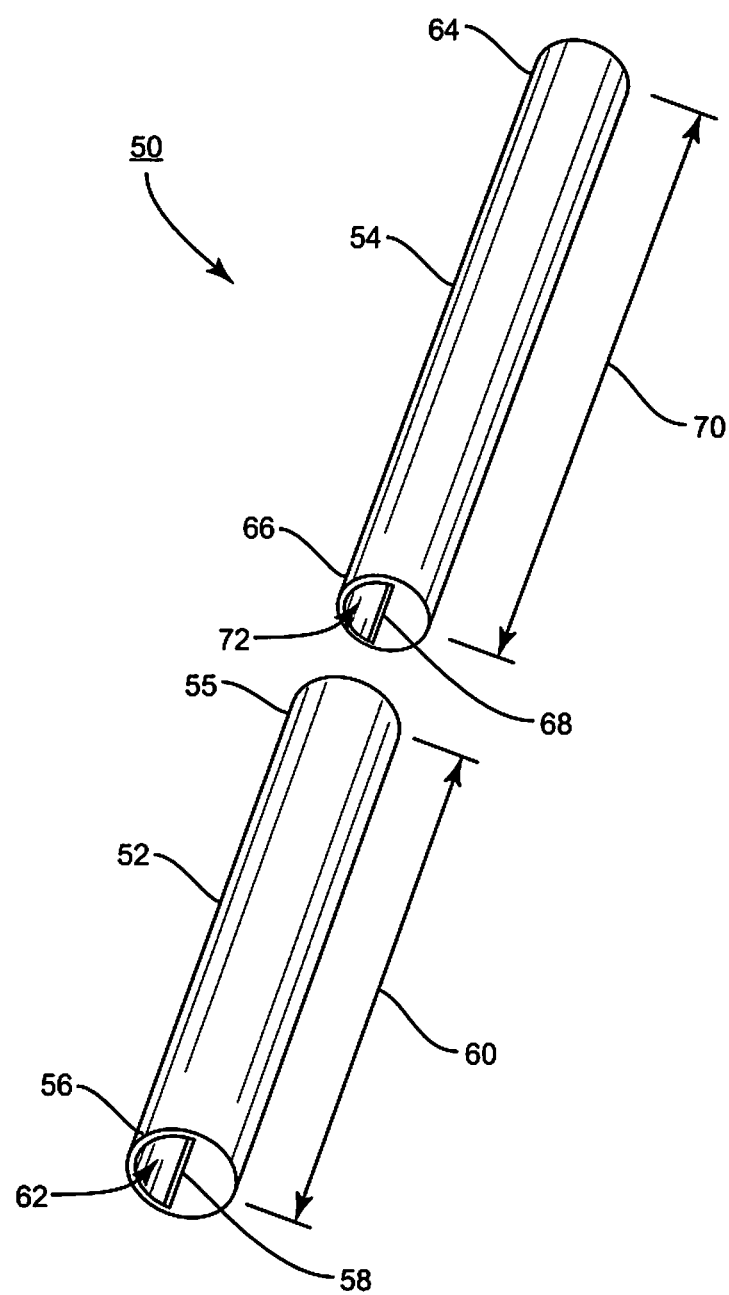
FIG. 2 illustrates an exploded perspective view of an exemplary embodiment of the secondary cutting implement of the present disclosure.

FIG. 2 illustrates a first exemplary embodiment of a secondary cutting implement 50 according to the present disclosure. The secondary cutting implement 50 is useful for trimming a graft (e.g. graft 80 explained below) being harvested from the quadriceps tendon 36, such as occurs when the cutting implement of the previously incorporated '562 application is used to cut a graft from the quadriceps tendon 36. The secondary cutting implement 50 has a first element 52, which is hollow and has a first handle end 55 and a first distal end 56. The first distal end 56 includes a first blade element 58. The first blade element 58 is positioned perpendicular to a longitudinal axis 60 of the first element 52. The first blade element 58 may be integrally formed with the body of the first element 52 or fixedly secured thereto. In an exemplary embodiment, the first element 52 is adapted to be reusable while the first blade element 58 is removably affixed thereto such that it can be replaced readily. Thus, the first blade element 58 may be considered disposable or reusable as desired. The first blade element 58 extends, in an exemplary embodiment, approximately halfway across first distal end 56 (e.g., covering approximately 45-55% (and in an exemplary embodiment approximately 51%) of the area of the first distal end 56) and partially defines a first aperture 62 through which a graft may be threaded as explained in greater detail below. In an exemplary embodiment, the first element 52 is made from a metal such as surgical stainless steel (e.g., made out of chromium, nickel, molybdenum, and/or titanium) such as 316L, 316LVM and/or compliant with ASTM F138. In an alternate embodiment, the first element 52 is made from a polymer based material. The first blade element 58 may be made from surgical steel, glass, obsidian, diamond, or the like as desired. In an exemplary embodiment, the first element 52 may be approximately 100 mm long.

The second element 54, which is hollow and has a second handle end 64 and a second distal end 66. The second distal end 66 includes a second blade element 68. The second blade element 68 is positioned perpendicular to a longitudinal axis 70 of the second element 54. The second blade element 68 may be integrally formed with the body of the second element 54 or fixedly secured thereto. In an exemplary embodiment, the second element 54 is adapted to be reusable while the second blade element 68 is removably affixed thereto such that it can be replaced readily. Thus, the second blade element 68 may be considered disposable or reusable as desired. The second blade element 68 extends, in an exemplary embodiment, approximately halfway across second distal end 66 (e.g., covering approximately 45-55% (and in an exemplary embodiment approximately 51%) of the area of the second distal end 66) and at least partially defines a second aperture 72 through which a graft may be threaded as explained in greater detail below. In an exemplary embodiment, the second element 54 is made from a metal such as surgical stainless steel (e.g., made out of chromium, nickel, molybdenum, and/or titanium) such as 316L, 316LVM and/or compliant with ASTM F138. In an alternate embodiment, the second element 54 is made from a polymer based material. The second blade element 68 may be made from surgical steel, glass, obsidian, diamond, or the like as desired. In an exemplary embodiment, the second element 54 may be approximately 120 mm long and 23 mm in interior diameter. The first element 52 may be sized such that its interior diameter is just large enough to fit around the exterior diameter of second element 54.

By design, the first element 52 is shorter than the second element 54, and the second element 54 telescopingly fits within the first element 52 such that the second handle end 64 extends out past the first handle end 55 so as to facilitate manipulation of the second element 54 within the first element 52.

In an exemplary embodiment, the handle ends 55 and 64 may be abraded, knurled, or otherwise textured to provide a firm gripping surface. In an alternate embodiment, there may be an explicit handle attached to or formed on the handle ends 55 and 64 to make manipulation and grip more natural.

Figure 3A:
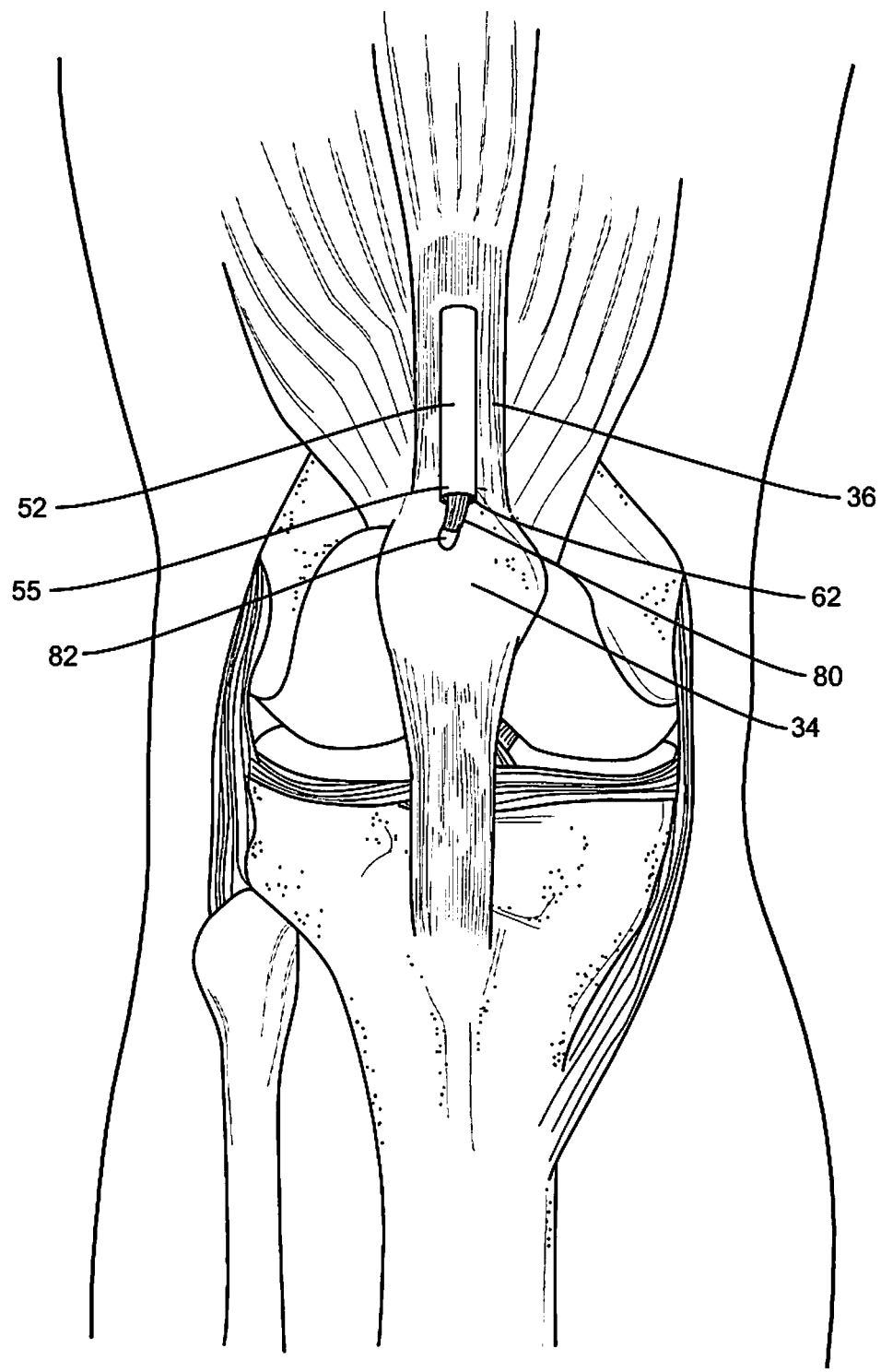
FIGS. 3A-3F schematically illustrate operation of the secondary cutting element.
Figure 3B:
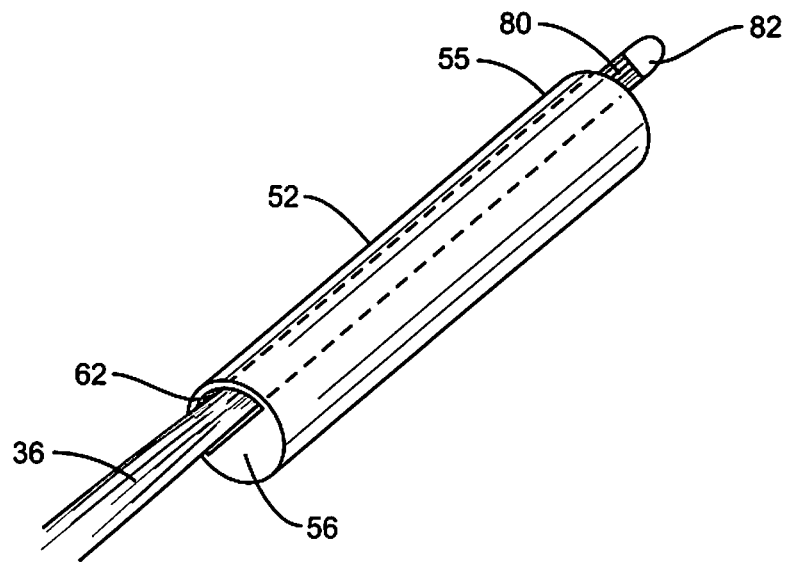
Figure 3C:
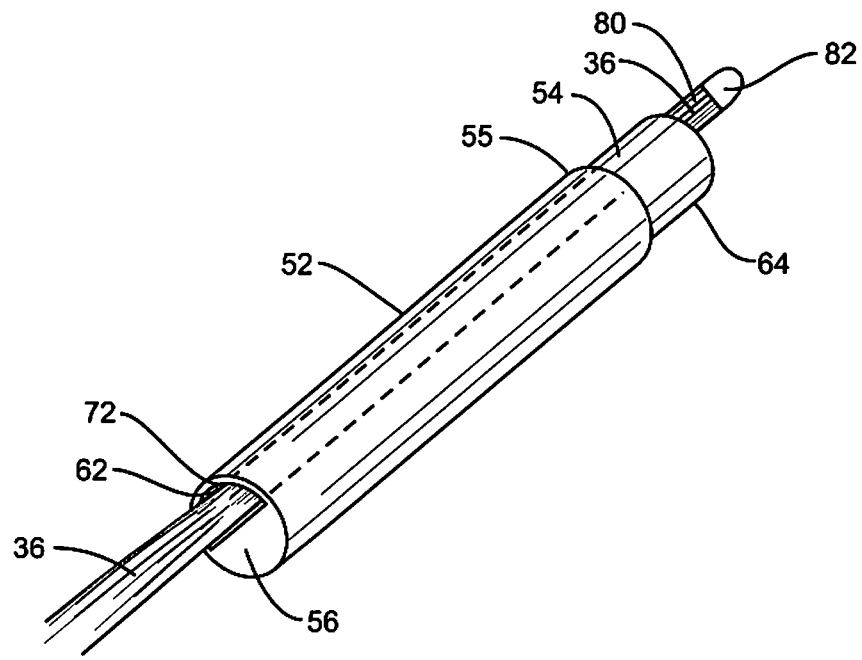
Figure 3D:
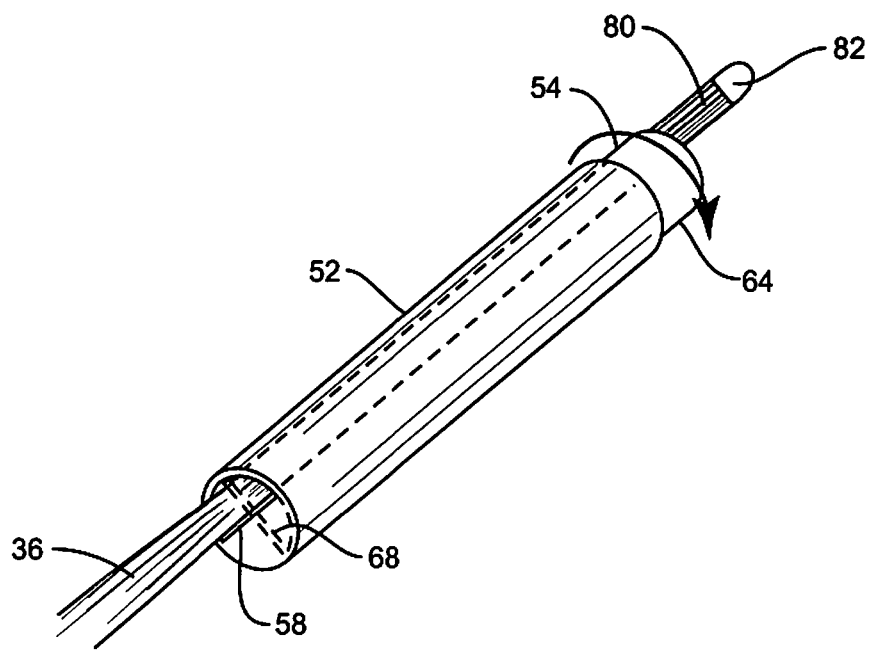
Figure 3E:
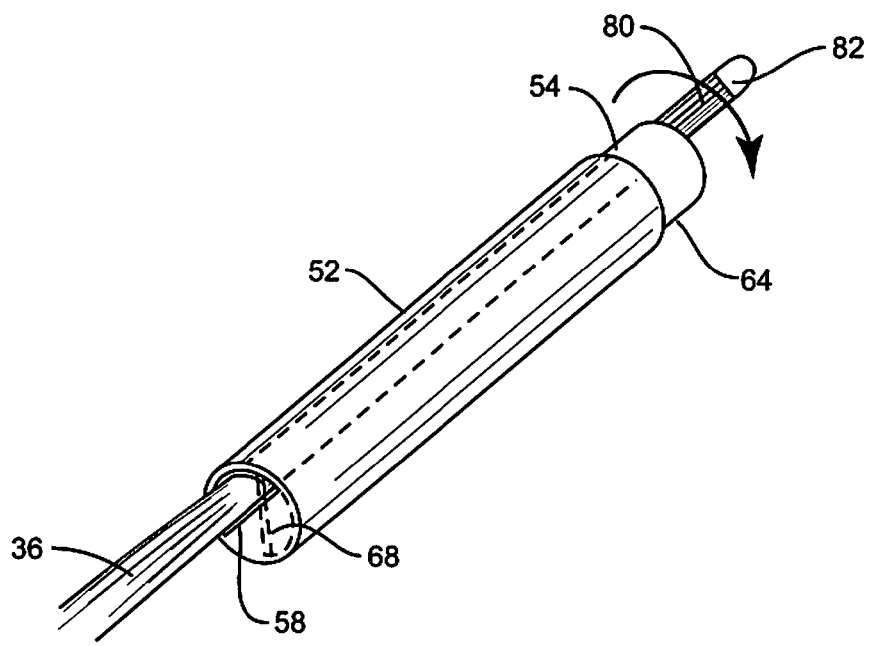
Figure 3F:
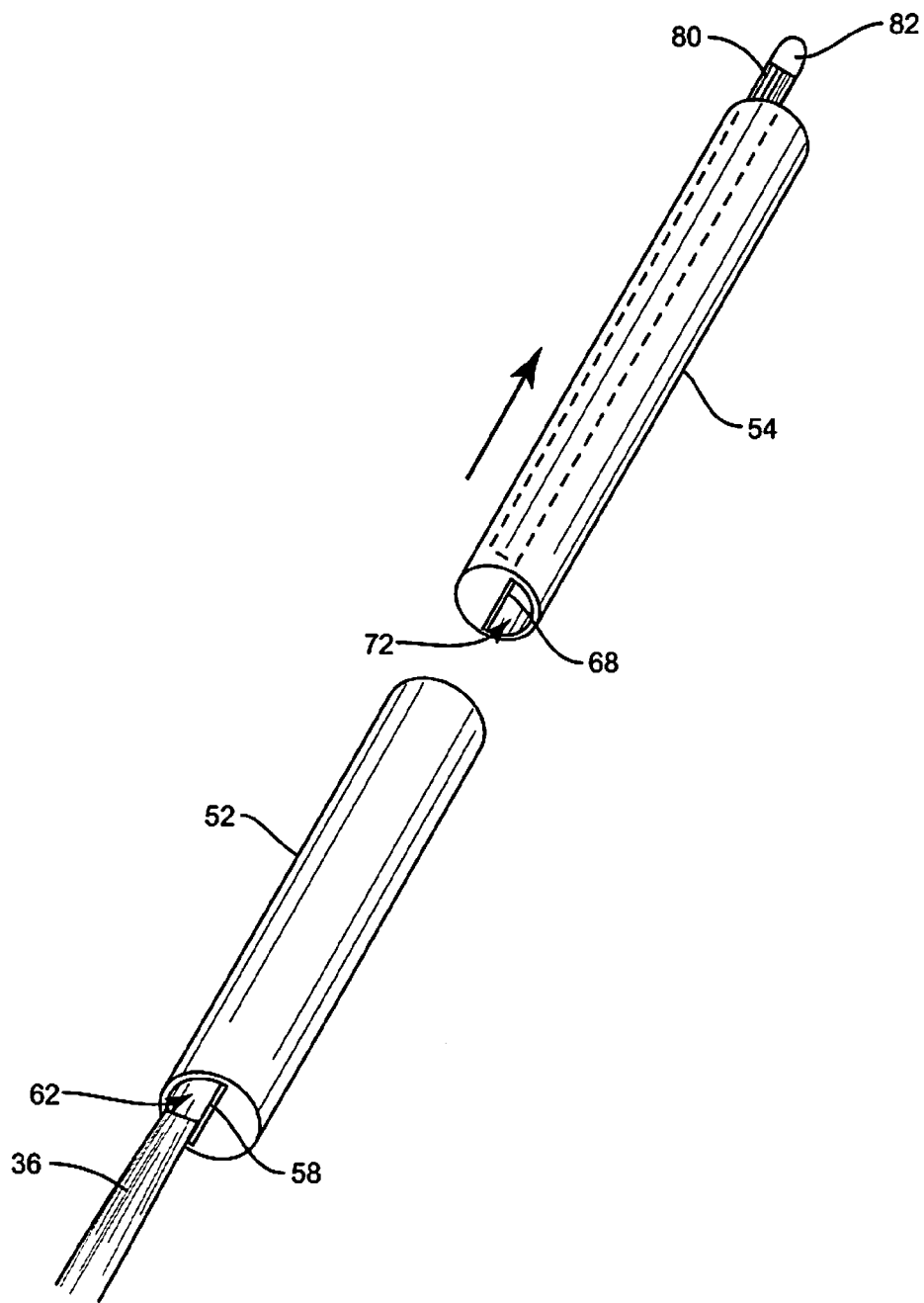
Figure 4:
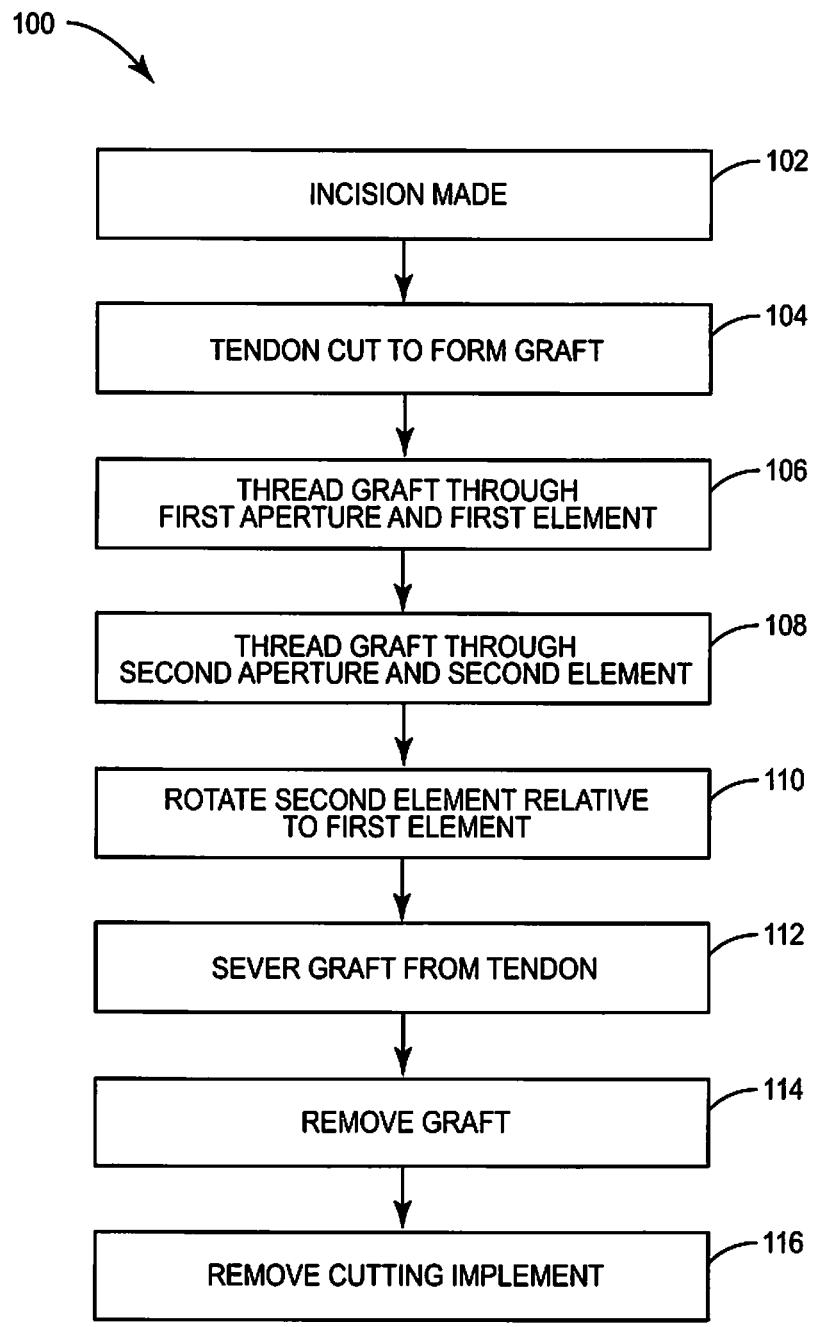
FIG. 4 illustrates a flow chart describing the operation of the secondary cutting element.

FIGS. 3A-3F illustrate a technique of using the secondary cutting implement 50 as further explained in the flowchart of FIG. 4. The process 100 of harvesting the graft 80 begins with the incision being made (block 102) and the tendon being cut to form the graft 80 (block 104). As explained in the previously incorporated '562 application, the graft 80 may be created from the quadriceps tendon 36, and may include a terminal bone plug formed from the patella.

Once the graft 80 is cut from the quadriceps tendon 36, the cutting implement is removed and the first element 52 is threaded through the first aperture 62 (block 106), through the hollow portion of the first element 52 and out the first handle end 55. Thus, the interior dimensions of the hollow portion of the first element 52 should be sized so as to accommodate the graft 80 and the bit of patella 82. Likewise, the size of the first aperture 62 should be sufficient to pass both the graft 80 and the bit of patella 82.

Note that as used herein "threaded through" or similar phrases draws analogy to threading a needle, and does not refer to the threads on a screw.

The graft 80 may then be threaded through the second aperture 72 and the second element 54 (block 108 and FIG. 3C). Note that if the apertures 62 and 72 are aligned and the second element 54 is already positioned within the first element 52, the graft 80 may be threaded through the first and second elements 52, 54 concurrently. As is seen in FIG. 3C, the second handle end 64 extends past the first handle end 55. Likewise, at least initially, the apertures 62 and 72 are aligned to allow the graft 80 to pass therethrough.

The second element 54 is then rotated relative to the first element 52 (block 110, FIGS. 3D & 3E). As the two elements 52 and 54 are rotated relative to one another, the blade elements 58 and 68 rotate to one another and effectively close the aperture through which the graft 80 has been passed. This allows the blade elements 58 and 68 to scissor together, thereby cutting the graft 80. Once the rotation has been effectuated sufficiently, the graft 80 is severed (block 112).

The graft 80 is then removed (block 114) as well as the cutting implement 50 (block 116, FIG. 3F). Then the graft 80 may be used to repair the ACL as desired.

Figure 5:
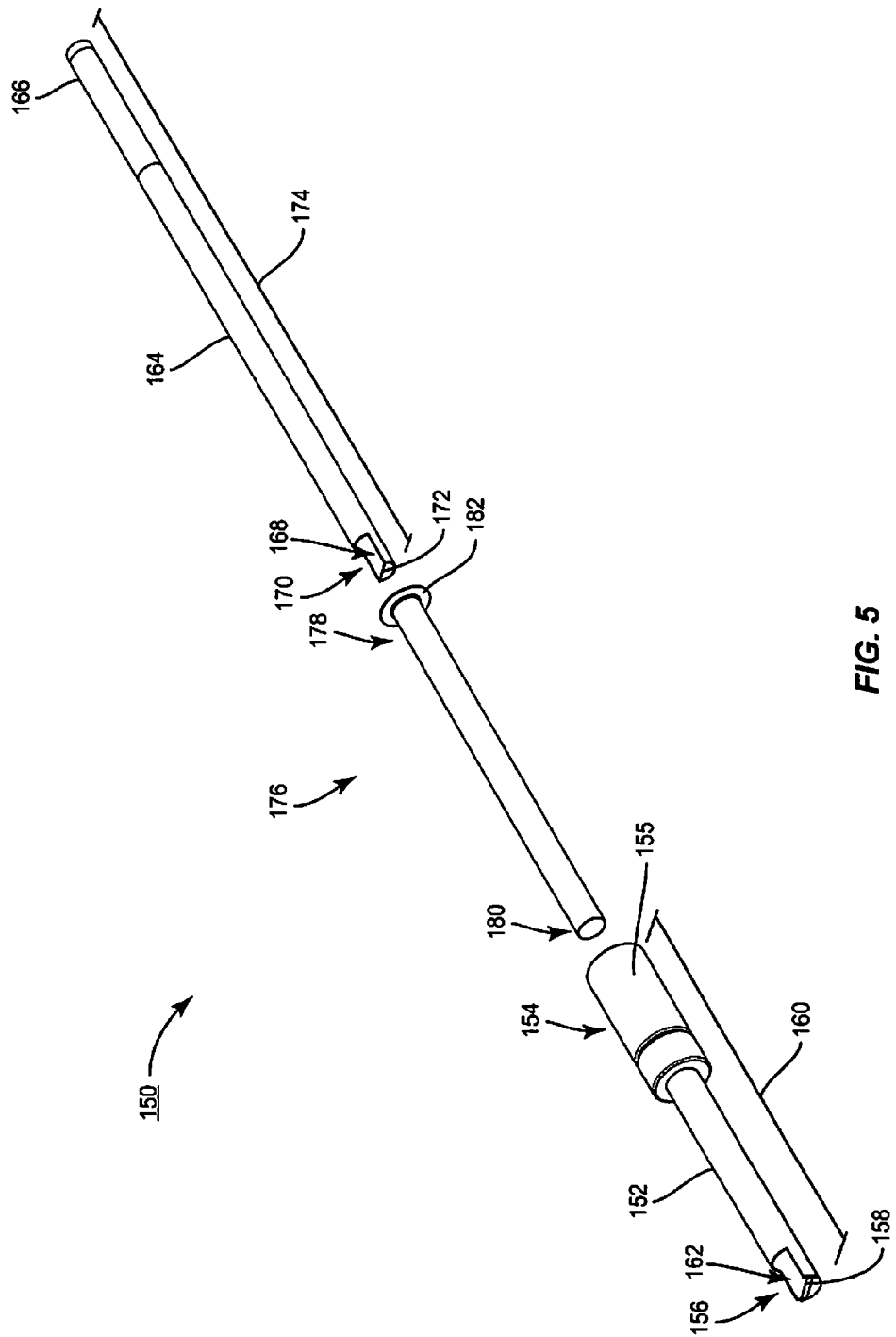
FIG. 5 illustrates an exploded perspective view of an exemplary embodiment of the secondary cutting implement of the present disclosure.

In an alternate embodiment, the second cutting element may be eliminated. In this regard, an exemplary embodiment of a secondary cutting implement 150 is illustrated in a perspective exploded format in FIG. 5. The secondary cutting implement 150 has a first element 152, which is hollow and has a first handle end 154 and a first distal end 156. The first handle end 154 may be encapsulated in a resilient polymeric annulus 155 which may be textured or knurled to provide a secure grip. The first distal end 156 includes a blade element 158. The blade element 158 is positioned perpendicular to a longitudinal axis 160 of the first element 152. The blade element 158 may be integrally formed with the body of the first element 152 or fixedly secured thereto. In an exemplary embodiment, the first element 152 is adapted to be reusable while the blade element 158 is removably affixed thereto such that it can be replaced readily. Thus, the blade element 158 may be considered disposable or reusable as desired. The blade element 158 extends, in an exemplary embodiment, approximately halfway across first distal end 156 (e.g., covering approximately 45-55% (and in an exemplary embodiment approximately 51%) of the area of the first distal end 156) and partially defines a first aperture 162 through which a bone plug portion of a graft 80 may be threaded as explained above. The first distal end 156 further includes a cut out portion which further defines the first aperture 162. In an exemplary embodiment, the cut out portion is an L-shaped section removed from the cylinder of the body of the first element 152. The cut out section may be approximately 25 mm long and remove about 30-50% (and in an exemplary embodiment 49%) of the circumference of the first distal end 156. The cutout portion provides more room for the first aperture 162 to accommodate the bone plug.

In an exemplary embodiment, the first element 152 is made from a metal such as surgical stainless steel (e.g., made out of chromium, nickel, molybdenum, and/or titanium) such as 316L, 316LVM, and/or compliant with ASTM F138. In an alternate embodiment, first element 152 is made from a polymer based material. The blade element 158 may be made from surgical steel, glass, obsidian, diamond, or the like as desired. In an exemplary embodiment, the first element 152 may be approximately 200 mm long.

The secondary cutting implement 150 further includes a second element 164, which is hollow and has a second handle end 166 and a second distal end 168. Instead of a cutting element, the second element 164 has a blunt edge 172. The blunt edge 172 is positioned perpendicular to a longitudinal axis 174 of the second element 164. The blunt edge 172 may be formed from the same material as the body of the second element 164 or may be removably affixed to the body. The blunt edge 172 extends, in an exemplary embodiment, approximately half way across second distal end 168 (e.g., covering approximately 45-55% (and in an exemplary embodiment approximately 51%) of the area of the second distal end 168) and at least partially defines a second aperture 170. The second distal end 168 further includes a cut out section, which, in an exemplary embodiment is L-shaped and helps define the second aperture 170. The cut out section facilitates threading the bone plug portion of the graft 80 through the hollow portion of the second element 164. The cut out section may be approximately 25 mm long In an exemplary embodiment, the second element 164 is made from a metal such as surgical stainless steel (e.g., made out of chromium, nickel, molybdenum, and/or titanium) such as 316L, 316LVM, and/or compliant with ASTM F138. In an alternate embodiment, second element 164 is made from a polymer based material. In an exemplary embodiment, the second element 164 may be approximately 460 mm long. By design, the second element 164 has a smaller radius than the first element 152 such that the second element 164 may telescopingly fit within the first element 152. Likewise, by design the first element 152 is shorter than the second element 164 such that that the second handle end 166 extends out past the first handle end 154 so as to facilitate manipulation of the second element 164 within the first element 152.

In addition to first element 152 and second element 164, the secondary cutting implement 150 may further (but optionally) include a third element 176 which is provided to lend stability to the secondary cutting implement 150. In particular, the third element 176 may be included such that on insertion, the third element 176 closes the cutaway or notches in the first element 152 and the second element 164, so as to improve cutting when the notches are partially aligned. That is, with the cut outs on the first and second elements 152, 164, there is a point in the counter-rotation of the elements 152, 164 where the graft 80 is not supported, which makes cutting the tendon difficult. Thus, the third element 176 may be telescopingly inserted between the first element 152 and the second element 164 and provide support for the tendon during cutting. The third element 176 includes a third handle end 178 and a third distal end 180. The third handle end 178 includes a flange 182 that prevents over-insertion of the third element 176 into the first element 152 and provides a method of maintaining forward pressure on the first element 152 to improve its effectiveness. In an exemplary embodiment, the third element may be approximately 280 mm long.

Figure 6:
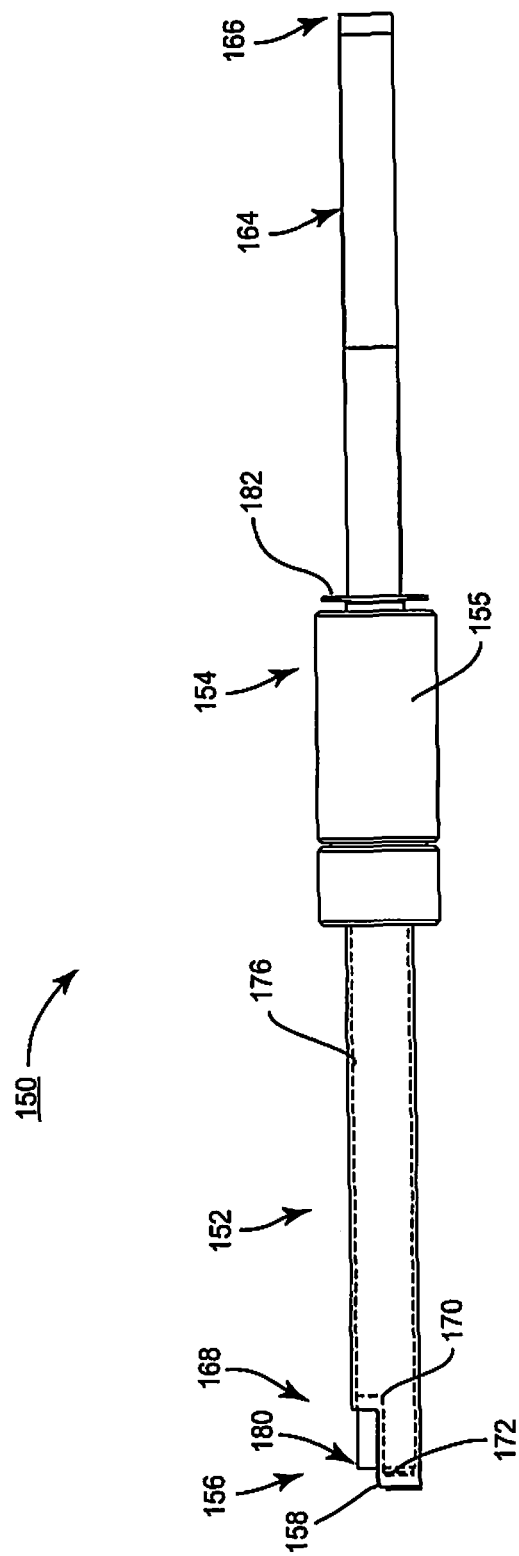
FIG. 6 illustrates a side view of the secondary cutting implement of FIG. 5.

FIG. 6 illustrates the secondary cutting implement 150 assembled. The distal ends 156, 168 and 180 are all proximate one another as the elements 152, 164, 176 telescopingly fit within one another (second inside third inside first). The cut outs on the first and second elements 152, 164 line up and allow the bone plug to pass through readily. Additionally, the user may grasp the resilient polymeric annulus 155 and the handle end 166 to rotate the first and second elements 152, 164 relative to one another so as to cause the blade element 158 to engage and sever the tendon. The flange 182 may be used to slide the third element 176 back and forth as needed (i.e., it may be retracted during insertion of the bone plug and tendon and then slid forward once the threading is done and the operator is ready to begin cutting).

Figure 7:
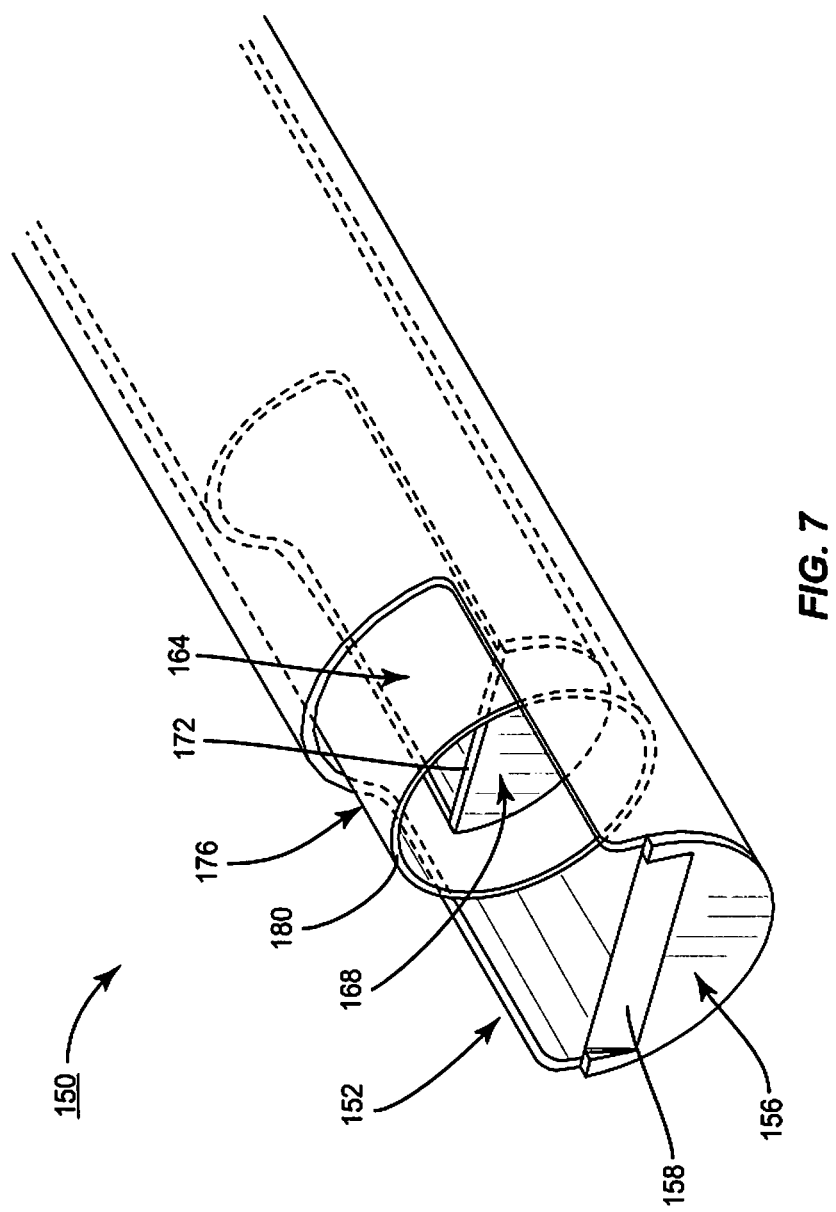
FIG. 7 illustrates a perspective close up of the cutting end of the secondary cutting implement of FIG. 5.
Figure 8:
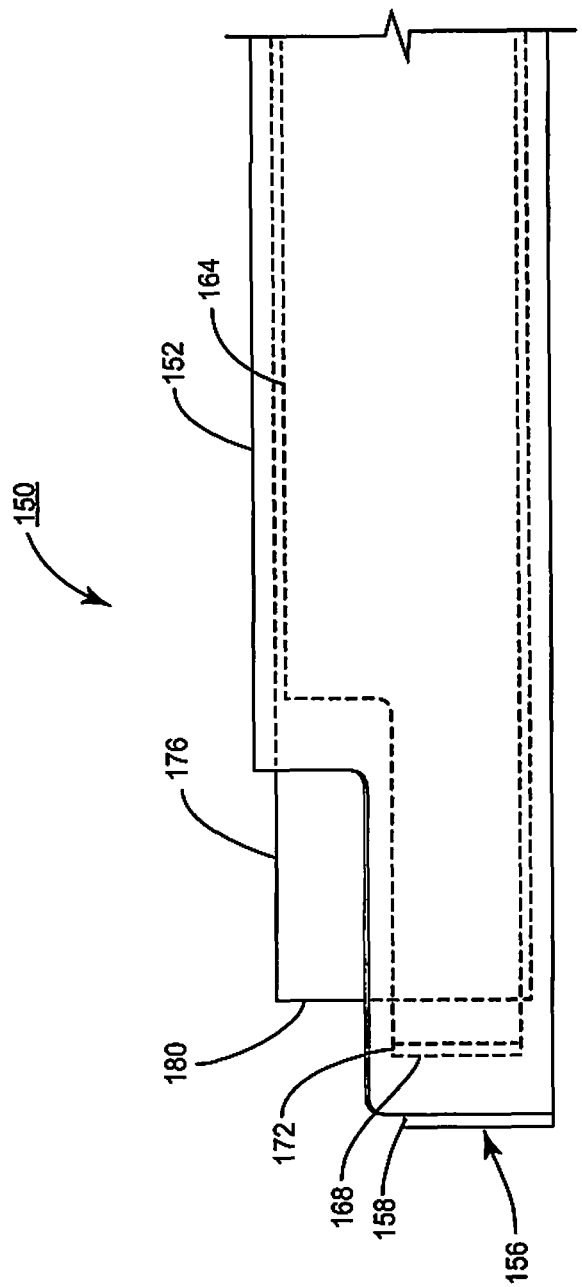
FIG. 8 illustrates a side close up of the cutting end of the cutting implement of FIG. 5.
Figure 9:
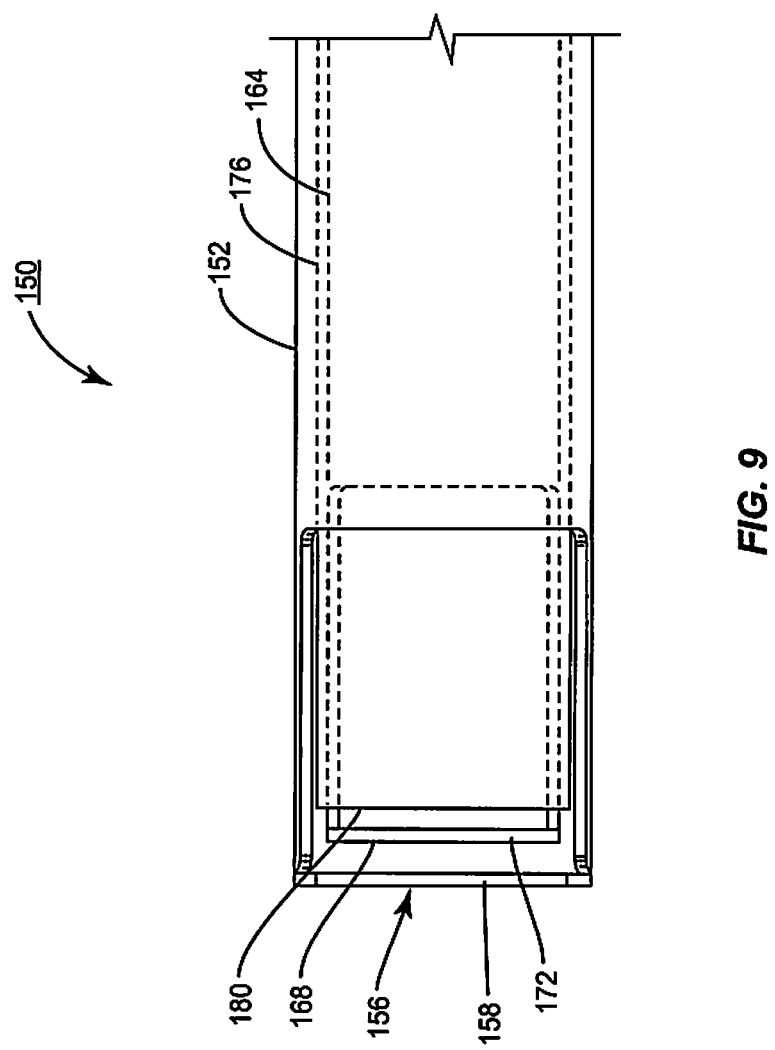
FIG. 9 illustrates a top close up of the cutting end of the cutting implement of FIG. 5.

FIGS. 7-9 illustrate a close up of the distal ends 156, 168, and 180 of the first, second and third elements 152, 164, 176 respectively. As previously explained, the blade element 158 is available to interoperate against the blunt edge 172 to cut the tendon and the third element 176 provides support for the tendon during the cutting.

While the illustrated embodiment has the blade element 158 and the blunt edge 172, these two may be reversed. That is, in such alternate embodiment, the first element 152 has a blunt edge at the first distal end 156 and the second element 164 has a blade element at the second distal end 168.

While the present disclosure has focused on the secondary cutting implement 150 being used to cut the quadriceps tendon as part of an operation to repair an injury to an ACL, the present disclosure is not so limited. The secondary cutting implement 150 may be used in other graft harvesting operations or for other purposes as needed or desired.

Those skilled in the art will recognize improvements and modifications to the embodiments of the present disclosure. All such improvements and modifications are considered within the scope of the concepts disclosed herein and the claims that follow.

What is claimed is:

1. A surgical instrument comprising:
  a first hollow element comprising a first longitudinal axis, a first distal end and a first handle end, the first distal end comprising a first blade element perpendicular to the fist longitudinal axis; and
  a second hollow element comprising a second distal end and a second handle end, the second distal end comprising a blunt edge, the blunt edge perpendicular to the fist longitudinal axis; and
  wherein the first hollow element is sized relative to the second hollow element such that the second hollow element telescopingly fits within the first hollow element and is adapted to rotate therewithin in such a manner that rotation of the second hollow element relative to the first hollow element causes the first blade element and the blunt edge to interoperate to cut a workpiece.

2. The surgical instrument of claim 1 wherein the first hollow element is tubular.

3. The surgical instrument of claim 1 wherein the second hollow element is tubular.

4. The surgical instrument of claim 1 wherein the first blade element at least partially defines a first aperture on the first hollow element such that the workpiece may be threaded through the first aperture and wherein the first aperture comprises a cut out portion.

5. The surgical instrument of claim 1 wherein the blunt edge at least partially defines a second aperture on the second hollow element such that the workpiece may be threaded through the second aperture and wherein the second aperture comprises a cut out portion.

6. The surgical instrument of claim 1 further comprising a third hollow element sized to fit in the first hollow element.

7. The surgical instrument of claim 6 wherein the second hollow element is sized to fit in the third hollow element.

8. The surgical instrument of claim 1 wherein the second hollow element is longer than the first hollow element.

9. The surgical instrument of claim 1 wherein the workpiece is a quadriceps tendon and the blade elements are adapted to cut the quadriceps tendon.

10. The surgical instrument of claim 1 wherein the first and second hollow elements are adapted to be inserted within a human body.

* * * * *